United States Patent
Mahmood

(10) Patent No.: US 12,204,622 B2
(45) Date of Patent: Jan. 21, 2025

(54) CONTROLLER, METHOD AND DATA PROCESSING APPARATUS

(71) Applicant: Prevayl Innovations Limited, Wilmslow (GB)

(72) Inventor: Tahir Mahmood, Wilmslow (GB)

(73) Assignee: Prevayl Innovations Limited, Wilmslow (GB)

( * ) Notice: Subject to any disclaimer, the term of this patent is extended or adjusted under 35 U.S.C. 154(b) by 250 days.

(21) Appl. No.: 17/627,397

(22) PCT Filed: Aug. 20, 2020

(86) PCT No.: PCT/GB2020/052000
§ 371 (c)(1),
(2) Date: Jan. 14, 2022

(87) PCT Pub. No.: WO2021/032985
PCT Pub. Date: Feb. 25, 2021

(65) Prior Publication Data
US 2022/0261467 A1    Aug. 18, 2022

(30) Foreign Application Priority Data

Aug. 22, 2019 (GB) ..................................... 1912079
Aug. 22, 2019 (GB) ..................................... 1912099

(51) Int. Cl.
*G06F 21/32* (2013.01)
*A61B 5/00* (2006.01)
(Continued)

(52) U.S. Cl.
CPC .............. *G06F 21/32* (2013.01); *A61B 5/002* (2013.01); *A61B 5/117* (2013.01); *A61B 5/6804* (2013.01); *G06F 21/36* (2013.01); *H04W 12/33* (2021.01)

(58) Field of Classification Search
CPC .... G06F 21/32; G06F 21/36; H04W 12/3361; A61B 5/117; A61B 5/6804
See application file for complete search history.

(56) References Cited

U.S. PATENT DOCUMENTS 4,917,109 A * 4/1990 Ruge ..................... A61F 5/3784
                                                       128/874
5,964,354 A * 10/1999 Skinner ................. B07C 5/3412
                                                      198/465.4
(Continued)

FOREIGN PATENT DOCUMENTS

CN          109344654           2/2019
GB          2586501 A            2/2021
(Continued)

OTHER PUBLICATIONS

GB Combined Search Report and Examination Report dated Jan. 28, 2020 of GB Application 1912079.9.
(Continued)

*Primary Examiner* — Ayoub Alata
(74) *Attorney, Agent, or Firm* — Haley Guiliano LLP

(57) ABSTRACT

A controller (161) for a device (16) comprises an identifier obtaining module (165) arranged to obtain an identifier for a garment worn by a user. The controller (161) comprises a biometric module (167) arranged to use the identifier to obtain a biometric identity for the user wearing the identified garment and determine an operational mode for the device (16) from the biometric identity. A command generation module (169) is operable to generate a control command for controlling the device (16) based on the operational mode. The biometric module (167) may determine whether the user identified by the biometric identity is authorised to operate the device (16). The control command may be generated based on this determination.

18 Claims, 8 Drawing Sheets

(51) Int. Cl.
*A61B 5/117* (2016.01)
*G06F 21/36* (2013.01)
*H04W 12/33* (2021.01)

(56) References Cited

U.S. PATENT DOCUMENTS

| | | | |
|---|---|---|---|
| 9,171,435 B2 * | 10/2015 | Bairaktaris | G08B 5/36 |
| 9,257,133 B1 | 2/2016 | Strand | |
| 9,762,581 B1 * | 9/2017 | Wang | H04L 63/102 |
| 10,021,569 B2 * | 7/2018 | Joo | H04W 12/084 |
| 10,022,613 B2 * | 7/2018 | Tran | G06Q 20/321 |
| 10,105,098 B2 * | 10/2018 | Wiebe | A61B 5/0015 |
| 10,789,590 B2 * | 9/2020 | Tran | H04L 9/3236 |
| 11,113,375 B2 * | 9/2021 | Alameh | H04W 4/023 |
| 11,830,340 B1 * | 11/2023 | Cull | A61B 5/117 |
| 2012/0086550 A1 * | 4/2012 | LeBlanc | G07C 9/37 340/5.82 |
| 2012/0130563 A1 * | 5/2012 | McBain | B64D 45/0059 701/3 |
| 2014/0337930 A1 * | 11/2014 | Hoyos | G06F 21/34 726/4 |
| 2015/0135310 A1 * | 5/2015 | Lee | H04W 12/065 726/20 |
| 2015/0179028 A1 * | 6/2015 | Bairaktaris | G08B 5/36 340/815.4 |
| 2015/0262230 A1 * | 9/2015 | Cypher | G06Q 30/0261 705/14.49 |
| 2015/0278498 A1 | 10/2015 | Hong et al. | |
| 2015/0317855 A1 * | 11/2015 | Sezan | G06F 21/35 340/5.52 |
| 2015/0363986 A1 * | 12/2015 | Hoyos | G07C 9/00571 340/5.61 |
| 2015/0381609 A1 * | 12/2015 | Dadu | H04W 4/80 726/9 |
| 2016/0057138 A1 * | 2/2016 | Hoyos | G06V 40/168 726/7 |
| 2016/0065571 A1 * | 3/2016 | Hoyos | H04L 63/0428 713/168 |
| 2016/0072802 A1 | 3/2016 | Hoyos | |
| 2016/0080936 A1 * | 3/2016 | Rachuri | H04W 12/065 726/7 |
| 2016/0086402 A1 * | 3/2016 | Black | G06F 21/6245 340/5.53 |
| 2016/0117544 A1 * | 4/2016 | Hoyos | H04N 5/33 348/78 |
| 2016/0162844 A1 * | 6/2016 | Rachuri | H04W 52/0251 705/7.19 |
| 2017/0060298 A1 * | 3/2017 | Hwang | A61B 5/6807 |
| 2017/0087371 A1 * | 3/2017 | Freeman | A61B 5/721 |
| 2017/0181703 A1 * | 6/2017 | Kaib | A61N 1/3943 |
| 2017/0244702 A1 * | 8/2017 | Jwa | H04L 63/10 |
| 2018/0000367 A1 * | 1/2018 | Longinotti-Buitoni | A41D 13/1281 |
| 2018/0177677 A1 * | 6/2018 | Pamplin | A61F 13/085 |
| 2018/0241864 A1 * | 8/2018 | Males | H04B 17/27 |
| 2019/0147151 A1 | 5/2019 | Scopis et al. | |
| 2019/0199717 A1 * | 6/2019 | Hoyos | H04B 1/385 |
| 2019/0313913 A1 * | 10/2019 | Fu | G16H 40/67 |
| 2020/0297063 A1 * | 9/2020 | Andon | H04W 4/80 |
| 2020/0334347 A1 * | 10/2020 | Hoyos | H04L 63/0861 |
| 2021/0315458 A1 * | 10/2021 | Chahine | A41D 1/002 |
| 2021/0365534 A1 * | 11/2021 | Alameh | H04L 63/0861 |
| 2022/0110822 A1 * | 4/2022 | Cooper | A41D 1/04 |
| 2022/0113799 A1 * | 4/2022 | Schorey | G06F 3/015 |

FOREIGN PATENT DOCUMENTS

| | | |
|---|---|---|
| KR | 10-2016-0135410 A | 11/2016 |
| WO | WO 2018194013 | 10/2018 |
| WO | 2021/032985 A1 | 2/2021 |

OTHER PUBLICATIONS

International Search Report and Written Opinion of PCT/GB2020/052000 dated Oct. 13, 2020.
U.S. Appl. No. 17/773,978, filed May 3, 2021.
Examination Report received in GB1916671.9, mailed Feb. 4, 2022.
Examination Report received in GB1916671.9, mailed Sep. 1, 2021.
International Search Report and Written Opinion received for PCT Patent Application No. PCT/GB2020/052898, mailed on Jan. 22, 2021, 10 pages.
International Search Report received in PCT/GB2020/052000 mailed Oct. 13, 2020.
Search and Examination Report received in GB1912079.9 mailed Jan. 28, 2020.
Search and Examination Report received in GB1916671.9, mailed Apr. 30, 2020.
Written Opinion received in PCT/GB2020/052000 mailed Oct. 13, 2020.

* cited by examiner

CONTROLLER, METHOD AND DATA PROCESSING APPARATUS

CROSS-REFERENCE TO RELATED APPLICATIONS

This application is a national stage application under 35 U.S.C. § 371 of International Application PCT/GB2020/052000, filed Aug. 20, 2020, which claims priority of GB Patent Applications 1912079.9, filed Aug. 22, 2019, and 1912099.7, filed Aug. 22, 2019. The disclosure of which are hereby incorporated by reference herein in their entireties.

BACKGROUND

The present invention is directed towards a controller, method and data processing apparatus. The present invention is directed determining operational modes for a device using biosignal data sensed by a wearable device such as a garment.

Garments incorporating sensors are wearable electronics which can be designed to interface with a wearer of the garment, and to determine information such as the wearer's heart rate, rate of respiration, activity level, and body positioning. Such properties can be measured with a sensor assembly that includes a sensor for signal transduction and/or microprocessors for analysis. Such garments are commonly referred to as 'smart clothing' and may be referred to as 'biosensing garments' if they measure biosignals. Typically, such garments are only able to communicate locally with a user phone via a short-range communication protocol such as NFC or Bluetooth. Typically, such garments are directly paired to a particular phone.

It would be desirable to provide a mechanism for controlling devices using biosignal data sensed by a wearable device such as a garment.

SUMMARY

According to the present disclosure there is provided a controller, method and data processing apparatus as set forth in the appended claims. Other features of the invention will be apparent from the dependent claims, and the description which follows.

According to a first aspect of the disclosure, there is provided a controller for controlling a device. The controller comprises an identifier obtaining module arranged to obtain an identifier for a garment worn by a user. The controller comprises a biometric module arranged to use the identifier to obtain a biometric identity for the user wearing the identified garment and determine an operational mode of the device from the biometric identity. The controller comprises a command generation module operable to generate a control command for controlling the device based on the determined operational mode.

The biometric identity may be obtained from biosignal data sensed by the garment.

The identifier for the garment may be an identifier for a removable electronics module of the garment.

Beneficially, the controller for a device can receive an identifier for a garment worn by a user and use this identifier to obtain the biometric identity of the user wearing the garment. This is then used to determine an operational mode for the device. For example, a first user may desire to operate the device in a first way and a second user may desire to operate the device in a second, different, way. The biometric identity may be obtained from biosignal data sensed by the garment. Obtaining the biometric identity from the biosignal data may or may not be performed by the controller. Beneficially, the controller/device may not be required to obtain biosignal data directly from the wearer of the garment such as via a fingerprint module integrated into the device. This simplifies the construction of the device and allows for biometric based control of a device to be performed in situations where it may be challenging for a user to directly input biometric information into the device.

The identifier may be received from the garment. The identifier obtaining module may be arranged to control the device to receive the identifier form the garment. The garment may transmit the identifier to the device. The identifier obtaining module may be arranged to control the device to receive the identifier over a wireless network. The identifier may be received over a near-field communication protocol, a wireless body area network, WBAN, a wireless personal area network, WPAN, or a wireless local area network, WLAN, communication protocol.

The WBAN is a wireless network protocol that supports real-time health monitoring and consumer electronics applications. An example of WBAN is the standard IEEE 802.15.6. The WPAN is a wireless network protocol that carries the personal area network over a low-powered, short-distance wireless network technology such as IrDA, Wireless USB, Bluetooth® or ZigBee®.

The garment and the device may communicate via a near-field communication protocol. That is, both the garment and the device may comprise a loop antenna. Electromagnetic induction may be induced between the two loop antennas when the garment and the device are brought into proximity with one another.

The garment may comprise a radio-frequency identification (RFID) tag comprising the identifier. The controller may be arranged to read the identifier from the RFID tag to obtain the identifier. The RFID tag may be a passive or an active RFID tag. The garment may comprise a short-range radio transmitter. The radio transmitter may be arranged to transmit a coded signal comprising the identifier to the device. The coded signal may encrypt the identifier.

The identifier obtaining module may be arranged to process an image containing the garment so as to determine the identifier for the garment. The device may comprise an image capturing device such as a camera which is controllable by the controller to capture an image of the garment. The image may be received from another device. The garment may comprise visual information that identifies the garment such as in the form of a barcode or QR code. That visual information may be in the form of a visual symbol which comprises the identifier. The identifier obtaining module may be arranged to process the image containing the garment to identify the visual symbol and obtain the identifier from the visual symbol. The identifier may be encoded into the visual symbol of the garment. The identifier obtaining module may be arranged to decode the visual symbol to obtain the identifier.

The biometric module may be operable to determine the operational mode of the device based on a user profile for the user identified by the biometric identity. The biometric module may be arranged to access a user profile for a user identified by the biometric identity. The user profile may be used to determine the operational mode of the device. The user profile may list one or more user preferences for the user in relation to operating the device. Beneficially, the device may be operated by different users. The present disclosure enables the operation of the device to be customised for each different user to reflect different user preferences and requirements. This customisation is enacted by identifying the user using the obtained biometric identity.

The operational mode may relate to whether the user has the authority to operate the device. The biometric module may be operable to determine the operational mode of the device by determining, from the biometric identity, whether the user has the authority to operate the device. The biometric module may be a biometric authentication module. The command generation module may be operable to generate the control command based on the determination of whether the user has the authority to operate the device. Beneficially, the controller for a device is able to receive an identifier for a garment worn by a user and use this identifier to determine whether the user is authorised to control the device. This enhances the security of the device.

The command generation module may be operable to generate a control command which restricts the device from performing an operation when the user is not authenticated as having the authority to operate the device. In this way, the device or one or more features of the device may be disabled when the user is not authenticated as having the authority to operate the device.

The command generation module may be operable to generate a control command which allows the device to perform an operation when the user is authenticated as having the authority to operate the device. In this way, the device or one or more features of the device may be enabled when the user is authenticated as having the authority to operate the device.

In some examples of the present disclosure, the device obtains biosignal data from the garment and processes the biosignal data to determine the biometric identity of the user. The biometric module may be arranged to use the identifier to access biosignal data sensed by the garment and process the accessed biosignal data to determine the biometric identity of the user.

The device may receive biosignal data from the garment. The device may be able to receive biosignal data from a plurality of different garments. The incoming biosignal data may include in the data, e.g. in a header of the data, the identifier identifying the garment. In this way, the controller may be able to use the identifier obtained by the identifier obtaining module to determine which incoming biosignal data to access. The incoming biosignal data may be stored in a data store accessible by the controller. The controller may be able to use the identifier obtained by the identifier obtaining module to determine which incoming biosignal data stored in the data store to access.

The device may not (directly) receive the biosignal data from the garment. Instead, the garment may transmit the biosignal data to a server over a wireless network and in most preferred cases a mobile network. The controller may control the device to communicate with the server to obtain the biosignal for the garment that is required to perform the biometric authentication. The biometric module may be arranged to control the device to transmit a request for biosignal data to the server. The request may comprise the identifier. The biometric authentication module may be arranged to control the device to receive, from the server, the biosignal data.

In other examples of the present disclosure, the device does not obtain biosignal data from the garment, but instead receives the biometric identity of the user either from the garment or from a server. The garment may be arranged to process biosignal data sensed by the garment to determine the biometric identity of the user wearing the garment. The garment may transmit the biometric identity to the device or to a server. The controller may access the biometric identity from the garment or the server.

The biometric module may be arranged to control the device to transmit a request for the biometric identity of the user wearing the garment to a server, and control the device to receive, from the server, the biometric identity. The request may comprise the obtained identifier. Beneficially, in this approach, the controller (and the device) does not directly have access to biosignal data. This enhances security as it restricts the distribution of the biosignal data and allows for third party devices to obtain the benefits of operational mode determination/biometric authentication based on a biometric identity of a user wearing a garment without allowing the third-party devices access to sensitive data.

The biometric module may be arranged to determine, from the biometric identity, whether the user has the authority to operate the device by determining whether the biometric identity of the user corresponds to a pre-stored biometric identity for an authorised user.

The biometric identity of the user may be a biometric characteristic of the user. That is, the biosignal data may be processed to obtain the biometric characteristic of the user. The controller may have access to a datastore that pre-stores biometric characteristics for one or a plurality of users associated with the device. These may be users that are authorised to operate the device. The biometric identity of the user may be a user identification (user ID). That is, the biosignal data may be processed to obtain the biometric characteristic of the user. The biometric characteristic may be compared to pre-stored biometric characteristics to determine the user ID. The user ID may then be compared to one or a plurality of pre-stored user IDs for users associated with the device. These may be users authorised to operate the device. A user may be authorised to control the device if their determined user ID matches one of the pre-stored user IDs. The pre-stored user IDs may be associated with information relating to how the user prefers to operate the device. This information may be used to determine an operational mode of a device.

The controller may be operable to control the device according to the generated control command.

The garment may transmit biosignal data to a data store. The biosignal data may be stored in a region of the data store associated with the identifier. The biometric module may be arranged to use the identifier to access biosignal data from the data store. The biosignal data may then be processed to determine the biometric identity for the user.

The garment may transmit the biometric identity to a data store. The biometric identity may be stored in a region of data store associated with the identifier. The biometric module may be arranged to use the identifier to access the biometric identity from the data store. The data store may be local to the device. The data store may be on or linked to a server. The device may transmit the identifier to the server.

The device may be a fitness device. The fitness device may be any form of exercise equipment such as any form of gym equipment. The fitness device may be a cardiovascular training device, strength training device, or weight training device. The fitness device may be an exercise bike, treadmill, cross trainer, rowing machine, body composition analyser device, or scales.

According to a second aspect of the disclosure, there is provided a device comprising the controller as disclosed in relation to the first aspect of the disclosure.

According to a third aspect of the disclosure, there is provided a computer implemented method. The method comprises obtaining an identifier for a garment worn by a user. The method comprises using the identifier to obtain a biometric identity for the user wearing the identified garment. The method comprises determining an operational mode for the device from the biometric identity. The method comprises generating a control command for controlling the device based on the determined operational mode. The determining the operational mode may comprise determining, from the biometric identity, whether the user has the authority to operate the device. The generating the control command may be based on the determination of whether the user has the authority to operate the device.

According to a fourth aspect of the disclosure, there is provided a data processing apparatus. The apparatus comprises a communicator arranged to obtain, from a device, an identifier for a garment worn by a user. The apparatus comprises a biosignal data accessing module operable to access biosignal data sensed by the garment identified by the identifier. The apparatus comprises a biometric identification module operable to determine from the biosignal data the biometric identity of the user wearing the garment. The communicator may be further arranged to transmit the biometric identity of the user to the device.

According to a fifth aspect of the present disclosure, there is provided a computer implemented method. The method comprises receiving, from a device, an identifier for a garment worn by a user. The method comprises accessing biosignal data sensed by the garment identified by the identifier. The method comprises determining, from the biosignal data, the biometric identity of the user wearing the garment. The method may further comprises transmitting the biometric identity of the user to the device.

According to a sixth aspect of the present disclosure, there is provided a data processing apparatus. The apparatus comprises a communicator arranged to obtain, from a device, an identifier for a garment worn by a user. The apparatus comprises a biosignal data accessing module operable to access biosignal data sensed by the garment identified by the identifier. The apparatus comprises a biometric identification module operable to determine from the biosignal data the biometric identity of the user wearing the garment. The apparatus comprises an operational mode module operable to determine an operational mode for the device from the biometric identity. The communicator may be further arranged to transmit, to the device, the result of the determination performed by the operational mode module. The operational mode module may comprise a biometric authentication module operable to determine whether the user has the authority to operate the device. That is, the operational mode does not need to be determined by the device in all examples of the present disclosure and may instead be determined by the data processing apparatus, e.g. a server.

According to a seventh aspect of the present disclosure, there is provided a computer implemented method. The method comprises obtaining, from a device, an identifier for a garment worn by a user. The method comprises accessing biosignal data sensed by the garment identified by the identifier. The method comprises determining from the biosignal data the biometric identity of the user wearing the garment. The method comprises determining an operational mode for the device from the biometric identity. The method may further comprise transmitting, to the device, the result of the determination. The determining the operational mode may comprise determining whether the user has the authority to operate the device.

According to an eighth aspect of the present disclosure, there is provided a data processing apparatus. The data processing apparatus comprises a communicator arranged to obtain, from a device, an identifier for a garment worn by a user. The data processing apparatus comprises a biosignal data accessing module operable to access biosignal data sensed by the garment identified by the identifier. The data processing apparatus comprises a biometric identification module operable to determine from the biosignal data the biometric identity of the user wearing the garment. The data processing apparatus comprises an operational mode module operable to determine an operational mode for the device from the biometric identity. The data processing apparatus comprises a control command generation module operable to generate a control command for controlling the device based on the determined operational mode. The communicator may be further arranged to transmit, to the device, the control command. The operational mode module may comprise a biometric authentication module. The biometric authentication module may be operable to determine from the biometric identity whether the user has the authority to operate the device. The control command generation module may be operable to generate a control command for controlling the device based on the determination of whether the user has the authority to operate the device. That is, the control command does not need to be determined by the device in all examples of the present disclosure and may instead be determined by the data processing apparatus, e.g. a server. Thus, the device may just transmit the identifier for the garment to the server and receive the control command from the server.

According to a ninth aspect of the present disclosure, there is provided a computer implemented method. The method comprises obtaining, from a device, an identifier for a garment worn by a user. The method comprises accessing biosignal data sensed by the garment identified by the identifier. The method comprises determining from the biosignal data the biometric identity of the user wearing the garment. The method comprises determining an operational mode for the device from biometric identity. The method comprises generating a control command for controlling the device based on the determined operational mode. The method may further comprise transmitting, to the device, the control command. The determining the operational mode may comprise determining whether the user has the authority to operate the device. The generating the control command may comprise generating a control command for controlling the device based on the determination of whether the user has the authority to operate the device.

According to a tenth aspect of the present disclosure, there is provided a computer program comprising instructions which, when the program is executed by a computer, cause the computer to carry out the method of the third, fifth, seventh or ninth aspect of the present disclosure.

According to an eleventh aspect of the present disclosure, there is provided a computer readable storage medium comprising instructions which, when executed by a computer, cause the computer to carry out the method of the third, fifth, seventh or ninth aspect of the present disclosure.

According to a twelfth aspect of the present disclosure, there is provided a system. The system comprises the data processing apparatus of the fourth, sixth or eighth aspect of the present disclosure. The system comprises a controller for controlling a device. The controller comprises an identifier obtaining module arranged to obtain an identifier for a garment worn by a user. The controller is operable to control a communicator of the device to transmit the identifier to the data processing apparatus. The controller may be the controller of the first aspect of the present disclosure. The system may further comprise the device. The system may further comprise the garment.

It may not be required to obtain the biometric identity in all aspects of the present disclosure. That is, the operational mode may be determined based on the identifier for the garment without performing a biometric identification procedure. Different garments may be associated with different operational modes of the device. The device or the server may have access to a database that links the different operational modes to different garments. The device or the server may use the identifier for the garment to determine the operational mode for the device.

The present disclosure is not limited to garments. The aspects of the present disclosure can be applied to any device. The device may be a mobile phone, tablet computer, gaming system, MP3 player, point-of-sale device, or wearable device such as a smart watch, necklace, bracelet, or glasses.

BRIEF DESCRIPTION OF THE DRAWINGS

Examples of the present disclosure will now be described with reference to the accompanying drawings, in which.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

Figure 1:
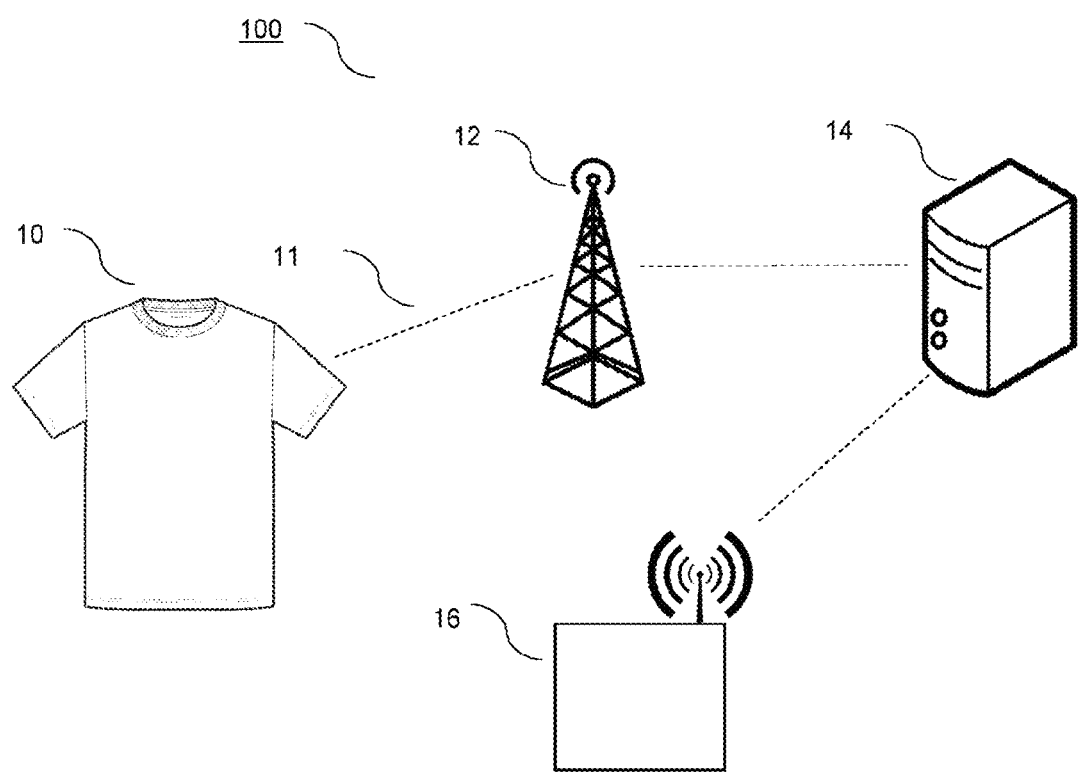
FIG. 1 shows a schematic diagram of an example system according to aspects of the present disclosure.

Referring to FIG. 1, there is shown a system 100 according to aspects of the present disclosure. The system 100 comprises garment 10, server 14 and device 16. The garment 10 transmits data over one or more channels 11 of a wireless network represented by base station 12. The wireless network 12 receives the data and provides the data to server 14.

In this example, the garment 10 is a biosensing garment 10. The biosensing garment 10 comprises one or more biosensing units, a communicator and a visual symbol. The visual symbol comprises, encoded therein, a code string that uniquely identifies the garment 10. The visual symbol is arranged such that it can be imaged by an image capturing device such as the camera of the device 16. The biosensing unit is for measuring one or more biosignals of the wearer. The biosensing unit is communicatively coupled to the communicator.

The device 16 comprises a controller in accordance with aspects of the present disclosure for controlling the device 16. The device 16 may communicate with the garment 10 and/or the server 14 over a wired or wireless network. That is, the device 16 may be a wireless device 16 or a wired device 16. A wireless device is intended to encompass any device 16 that connects to a wireless communication network. The wireless communication network is intended to encompass any type of wireless such as mobile/cellular networks used to provide mobile phone services. A wired device is intended to encompass any compatible wired technology computing device that can transmit and receive data over a wired communication network.

Figure 2:
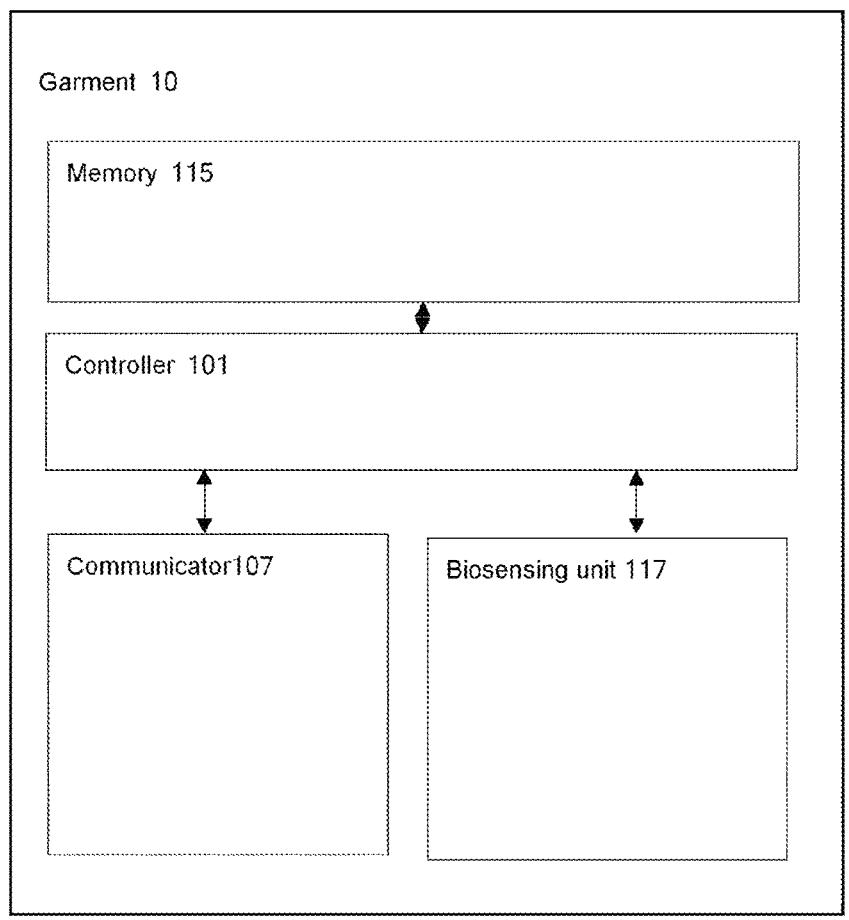
FIG. 2 shows a schematic diagram of an example garment according to aspects of the present disclosure.

Referring to FIG. 2, there is shown an example garment 10 according to aspects of the present disclosure. The garment comprises a controller 101, communicator 107, memory 115, and biosensing unit 117. The controller is operable to control the communicator 107 and biosensing unit 117 based on instructions stored in the memory 115.

The biosensing unit 117 refers to a (electronic) component that can measure a biosignal of the wearer. Here, "biosignal" may refer to any signal in a living being that can be measured and monitored. The term "biosignal" is not limited to electrical signals and can refer to other forms of non-electrical biosignals. The biosensing unit 117 may comprise one or more electrodes but is not limited to this arrangement. The biosensing unit 117 may be a textile-based biosensing unit 117. The terms "biosignal" and "biodata" are used synonymously throughout the specification.

The biosensing unit 117 may be use for measuring one or a combination of bioelectrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer's sweat.

The biomechanical measurements include blood pressure. The bioacoustics measurements include phonocardiograms (PCG). The biooptical measurements include orthopantomogram (OPG). The biothermal measurements include skin temperature and core body temperature measurements. The biosensing unit may comprise a radar unit.

The communicator 107 is arranged to transmit data to the server 14 via the wireless network 12 which may be a mobile network. The communicator 107 may be any form of communicator 107 operable to communicate data wirelessly via one or more base stations. The communicator 107 therefore provides wireless communication capabilities for the garment 10 and enables the garment 10 to communicate via one or more wireless communication protocols such as used for communication on: a wireless wide area network (WWAN), a wireless metroarea network (WMAN), a wireless local area network (WLAN), a wireless personal area network (WPAN), a near field communication (NFC), and a cellular communication network. The cellular communication network may be a fourth generation (4G) LTE, LTE Advanced (LTE-A), fifth generation (5G), sixth generation (6G), and/or any other present or future developed cellular wireless network.

The communicator 107 may comprise a baseband component. The garment 10 may comprise a secure element. The secure element may represent a removable universal integrated circuit card (UICC) or an embedded universal integrated circuit card (eUICC). The secure element may store multiple different eSIMs for accessing different mobile network operators (MNOs). Mobile network operators include virtual mobile network operations (VMNOs). The garment may be subscribed to multiple different MNOs, and the secure element may store an eSIM for each MNO to which the garment 100 is subscribed. The baseband component may include a baseband OS that is configured to manage hardware resources of the baseband component. The baseband component may itself comprise a processor, a memory, and radio components to effect communication over a wireless network. The garment 10 may comprise one or more external sensors which may measure one or more factors that are external to the wearer.

Figure 3:
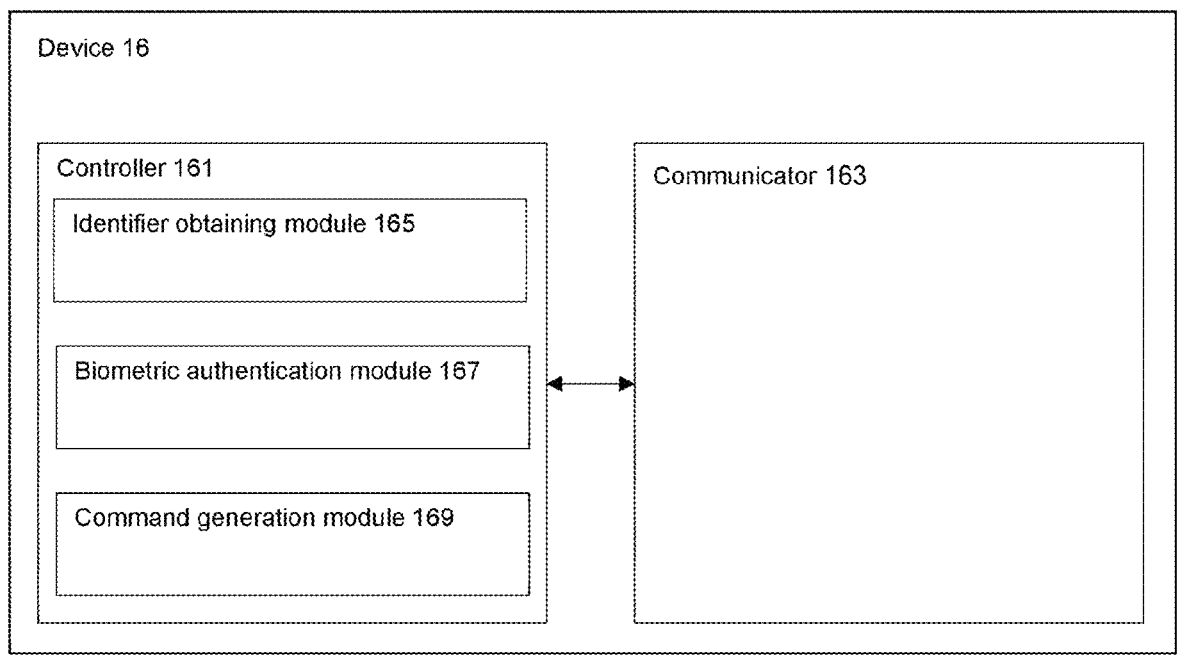
FIG. 3 shows a schematic diagram of an example device according to aspects of the present disclosure.

Referring to FIG. 3, there is shown a schematic diagram of an example device 16 according to aspects of the present disclosure.

The device 16 comprises a controller 161 and a communicator 163. The controller 161 is for controlling the device 16. The controller 161 comprises an identifier obtaining module 165 arranged to obtain an identifier for a garment 10 worn by a user. The controller 161 comprises a biometric authentication module 167 arranged to use the identifier to obtain a biometric identity for the user wearing the identified garment 10 and determine, from the biometric identity, whether the user has the authority to operate the device 16. The controller 161 comprises a command generation module 169 operable to generate a control command for controlling the device 16 based on the determination of whether the user has the authority to operate the device 16. The communicator 163 is arranged to communicate with the server 14.

Figure 4:
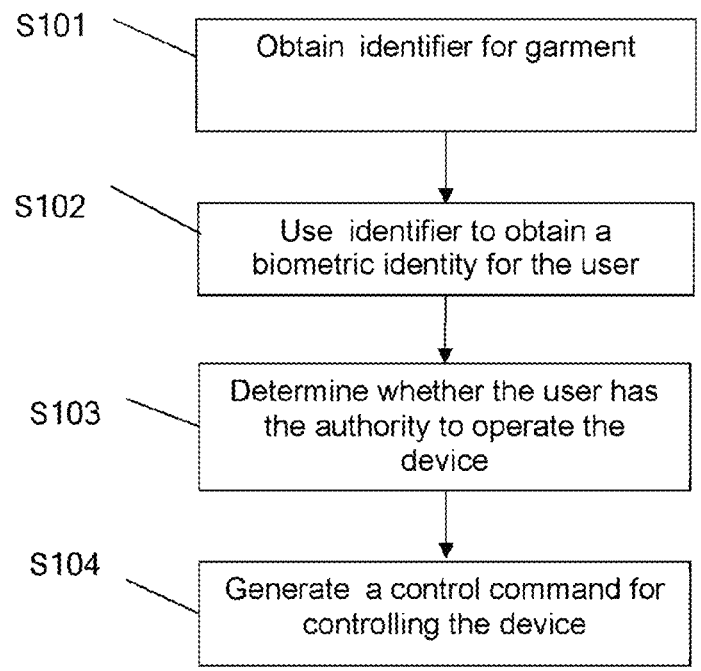
FIG. 4 shows a flow diagram for an example method according to aspects of the present disclosure.

Referring to FIG. 4, there is shown a method according to aspects of the present disclosure. The method may be performed by the controller 161 of the device 16 shown in FIG. 3. The method may be performed by the server 14. The method may be performed by the device 16 in cooperation with the server 14.

Step S101 of the method comprises obtaining an identifier for a garment worn by a user. Step S101 may be performed by the device 16 to be operated. That is, the device 16 may obtain the identifier for the garment 10. In an example, the garment 10 transmits an identifier for the garment 10 to the device 16. This could be performed using a wireless communication protocol, and in particular a local wireless communication protocol such as Near Field Communication (NFC). In another example, the device 16 reads an identifier on the garment 10. The device 16 could capture an image of an identifier on the garment 10. The identifier may be in the form of a visual symbol that has encoded therein a code string that uniquely identifies the garment. Step S101 may be performed by the server 14. The server 14 may receive the identifier for the garment 10 or from the device 16. That is, the device 16 may obtain the identifier and transmit the same to the server 14.

In example implementations, the unique identifier for the garment 10 is obtained from a visual symbol located on the garment 10 that comprises an encoded representation of a code string that uniquely identities the garment 10. The device 16 captures an image of the garment 10 so as to obtain an image of the visual symbol. The electronic device 16 digitises the visual symbol to generate a data string and, transmits the data string identification information to the server 14. In this way, unique identifier for the garment 10 that is obtained from the image is communicated to the server 14. The server 14 then decodes the data string to obtain the unique identifier for the garment 10.

Step S102 of the method comprises using the identifier to obtain a biometric identity for the user wearing the identified garment.

Step S103 of the method comprises determining, from the biometric identity, whether the user has the authority to operate the device.

Step S104 of the method comprises generating a control command for controlling the device based on the determination of whether the user has the authority to operate the device.

Figure 5A:
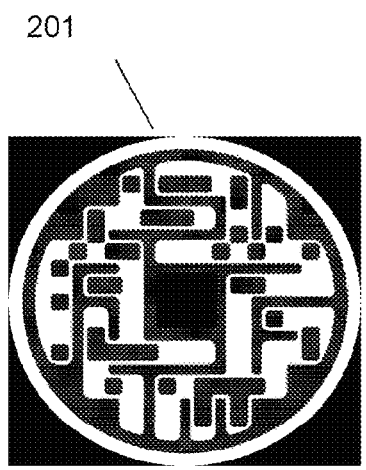
FIGS. 5A and 5B show example markers in accordance with aspects of the present disclosure.

Referring to FIG. 5A, there is shown an example marker 201 in accordance with the present disclosure. The marker 201 in this example is based on the Vcode® provided by VST Enterprises™ and comprises a visual symbol in the form of black marks upon white pathways. The black marks represent the characters in the code string. The visual symbol may additionally encode redundant information for error detection, correction, and uniqueness over different rotations of the marker. Beneficially, the marker 201 can also be used as an AR marker for motion tracking operations.

Figure 5B:
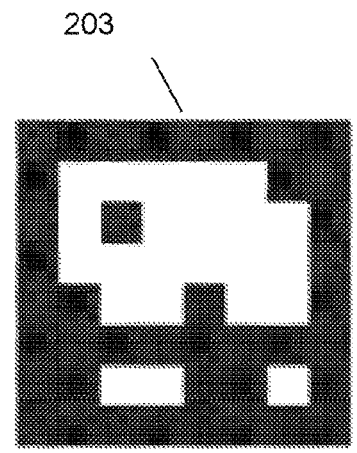

Referring to FIG. 5B, there is shown another example marker 203 in accordance with the present disclosure. The marker 203 in this example is derived from the AR marker system known as ARTag. The marker 203 comprises a visual symbol in the form of a 6×6 grid of black or white cells which represent 36 binary '0' or '1' symbols. The 36-bit sequence encodes the code string and may additionally encode redundant information for error detection, correction and uniqueness over the different rotations of the marker. Beneficially, the marker 203 can also be used as an AR marker for motion tracking operations.

Figure 6:
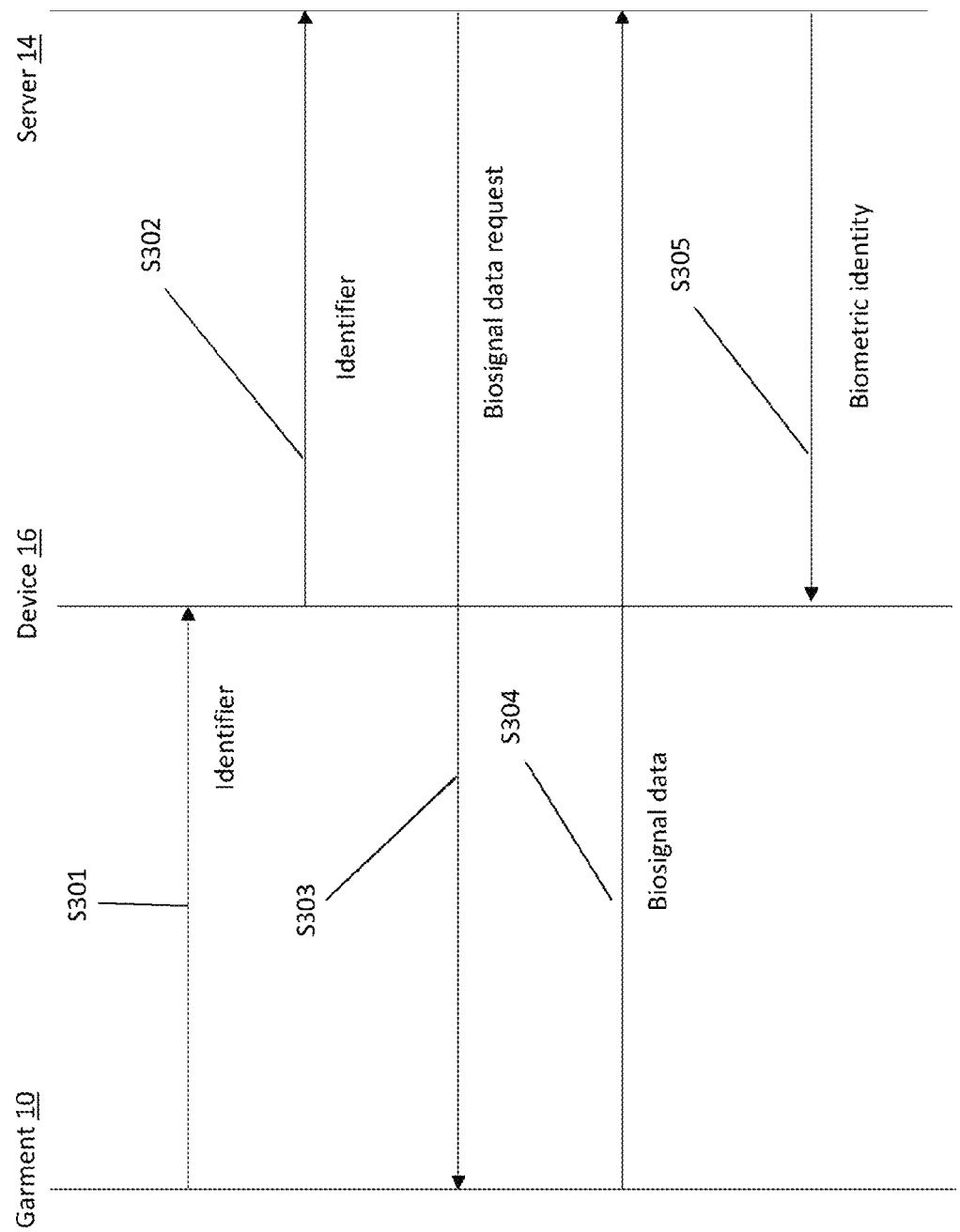
FIG. 6 shows a flow diagram for an example method according to aspects of the present disclosure.

Referring to FIG. 6, there is shown a signal flow diagram for an example method according to aspects of the present disclosure. In this example, the device 16 does not have access to the biosignal data and instead communicates with the server 14 to receive the biometric identity of the wearer of the garment 10. The example method is performed by the garment 10, device 16, and server 14.

In step S301, the garment 10 communicates an identifier to the device 16. The garment 10 may transmit the identifier over a wireless communication protocol. The garment 10 may transmit the identifier to the device 16 automatically if, for example, the garment 10 enters the vicinity of the device 16. For example, the garment 10 may be activated to communicate the identifier to the device 16 if the garment 10 is brought within two metres or less to the device 16.

In step S302, the device 16 communicates the identifier to the server 14. The identifier may be communicated along with information indicating to the server 14 that the device 16 requires the biometric identity of the wearer of the garment 100.

In step S303, the server 14 transmits a request for biosignal data for performing the biometric analysis from the garment 10 identified by the received identifier. This is not required in all examples, as instead the garment 10 may be continuously or repeatably transmit biosignal data to the server 14 when the garment 10 is worn.

In step S304, the garment 10 transmits biosignal data to the server 14. The server 14 determines the biometric identity for the user wearing the garment 10 based on the biosignal data.

In step S305, the server 14 transmits the determined biometric identity to the device 10 so that the controller 161 of the device 16 obtains the biometric identity for the garment. The controller 161 of the device 16 determines, from the biometric identity, whether the user has the authority to operate the device 16. The controller 161 of the device 16 generates a control command for controlling the device 16 based on the determination of whether the user has the authority to operate the device 16.

Figure 7:
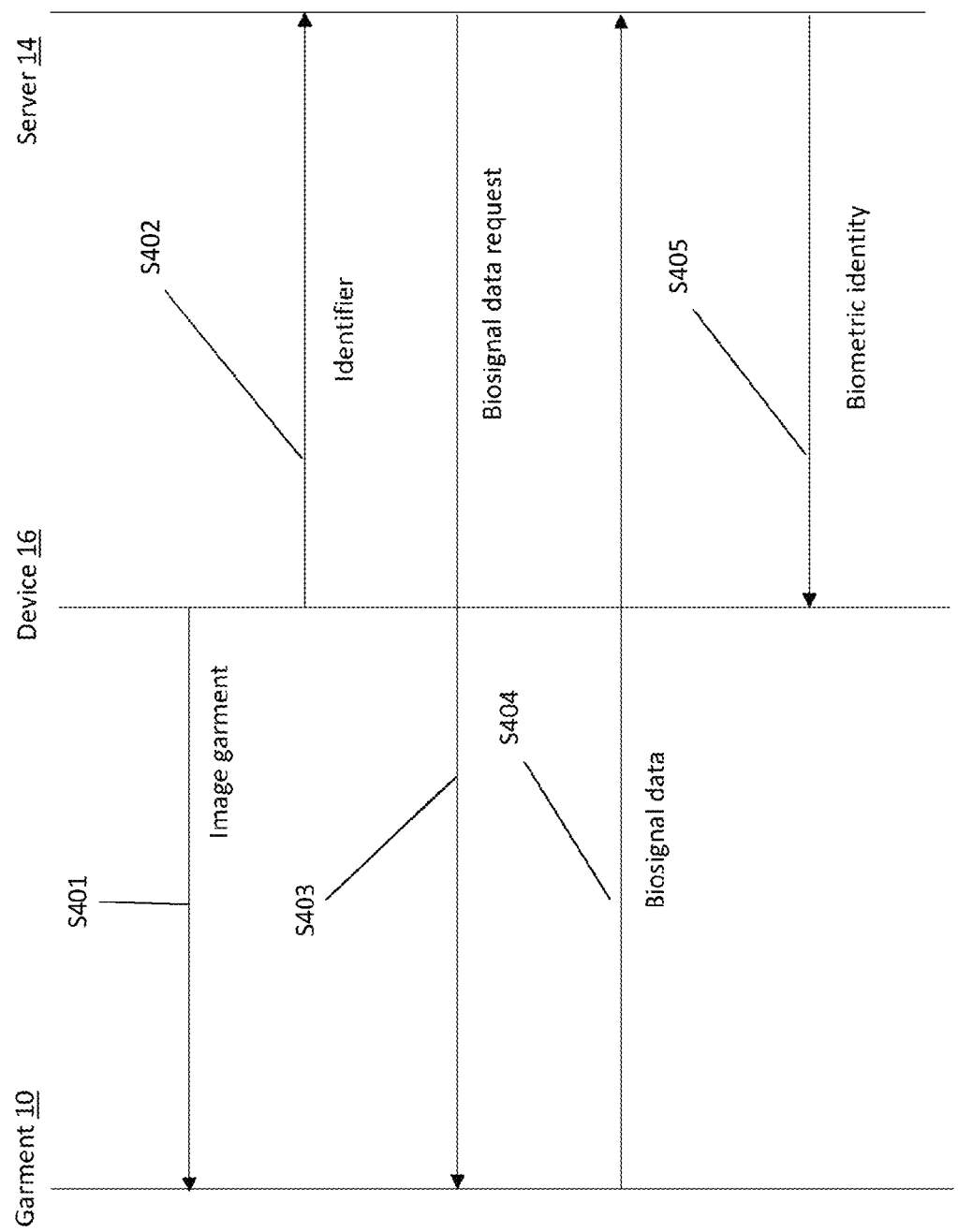
FIG. 7 shows a flow diagram for an example method according to aspects of the present disclosure.

Referring to FIG. 7, there is shown a signal flow diagram for an example method according to aspects of the present disclosure. In this example, the device 16 does not have access to the biosignal data and instead communicates with the server 14 to receive the biometric identity of the wearer of the garment 10. The example method is performed by the garment 10, device 16, and the server 14.

In step S401, the device 16 captures an image of the garment 10. The garment 10 comprises a visual symbol that comprises an encoded representation of a code string that uniquely identifies the garment. The device 16 digitises the visual symbol captured in step S401 to generate a data string identifier and, in step S402 transmits the data string identifier to the server 14. The server 14 decodes the received data string identifier to obtain the unique identifier for the garment 10. In this way, the server 14 is able to determine the identity of the garment 10 that the device 16 desires to use in a biometric authentication procedure.

In step S403, the server 14 transmits a request for biosignal data for performing the biometric analysis from the garment 10 identified by the received identifier. This is not required in all examples as the garment 10 may continuously or repeatably transmit biosignal data to the server 14 when the garment 10 is worn.

In step S404, the garment 10 transmits biosignal data to the server 14. The server 14 determines the biometric identity for the user wearing the garment 100 based on the biosignal data.

In step S405, the server 14 transmits the determined biometric identity to the device 16 so that the controller 161 of the device 16 obtains the biometric identity. The controller 161 of the device 16 determines, from the biometric identity, whether the user has the authority to operate the device 16. The controller 161 of the device 16 generates a control command for controlling the device 16 based on the determination of whether the user has the authority to operate the device 16.

In the above example disclosures, the biometric identity may be a user identification (user ID) that is unique to the user or may be a biometric characteristic that is subsequently compared with pre-stored biometric characteristics. The biometric characteristic may be any biometric characteristic as known in the art that may be used to uniquely identify the user. The biometric characteristic may include signals (e.g. electrical signals) from the heart which can be used to attain data points that are unique to the user. A user's heartbeat may be analysed using patterns gathered by Electrocardiograph, which records a heart's electric potential changes in time. A longer recording of heartbeat activity is called an electrocardiogram (ECG) and is recorded using one or more pairs of electrodes. Each pair measures the change of electrical potential between the points of contact of electrodes. This change is strongly correlated with heart and muscle activity of the subject as the heartbeat activity of the human body is stimulated through electrical impulses. The biometric characteristic may be obtained from bioimpedance measurements which may be obtained by performing different impedance measurements between different points on user's body at different frequencies. The biometric characteristic may include one or more of photoplethysmogram (PPG) data. The biometric identity may be obtained using at least one of blood oxygenation and heart rate variability (HRV) of the user which may be obtained from, amongst others, the PPG data. HRV varies from person to person and can therefore be used as a unique identifier for a user. The second derivative of photoplethysmogram (SDPPG) data obtained by processing PPG data may also be used to determine the biometric identity of the user as SDPPG data also varies from person to person. The present disclosure is not limited to the characteristics described above. Other characteristics such as gait analysis obtained from motion and position sensors incorporated into the garment may also be used to uniquely identify the user, for example.

In some examples, the garment 10 performs no or only a limited amount of processing on biosignals sensed by the biosensing units 117. The sensed biosignals (e.g. ECG and/or PPG signals) can be processed to determine biometric characteristics of the user wearing the garment. At least a component of the biosignals are transmitted to the server 14. The method comprises processing the received biosignals to generate a biometric characteristic of the user.

This may involve determining the heart rate variability or SDPPG data for example. The server 14 may transmit the determine biometric characteristic to the device 16. Alternatively, the server 14 may then compare the received biometric characteristic to one or more pre-stored biometric characteristics to determine a user identification for the garment. The server 14 may then transmit the user identification to the device 16 which determines whether the user identification relates to a user authorised to use the device. Alternatively, the server 14 may determine from the user identification whether the user is authorised to use the device 16 and may then transmit the result of the determination to the device 16.

In other examples, the garment 10 may perform some of the processing operations before transmitting data to the server 14. For example, a biometric identification module of the garment may comprise a biometric detection module arranged to process biosignals to generate a biometric characteristic of the user. The biometric characteristic may be the biometric identity that is transmitted by the garment 10 to the server 14 or the device 16. The server 14 or device 16 may then compare the received biometric characteristic to one or more pre-stored biometric characteristics to determine a user identification for the garment. The server 14 may determine if the user identification relates to a user that is authorised to operate the device 16. In other examples, the biometric identification module of the garment 10 may also comprise an ID recognition module. The ID recognition module of the garment 10 may compare the generated biometric characteristic to one or more pre-stored biometric characteristics stored on the garment to determine a user identification for the garment 10. In this example, the user identification can be considered as the biometric identifier that is transmitted to the server 14. The garment 10 may then transmit the user identification to the server 14 or device 16 which may then determine whether the user identification is for an authorised user.

Figure 8:
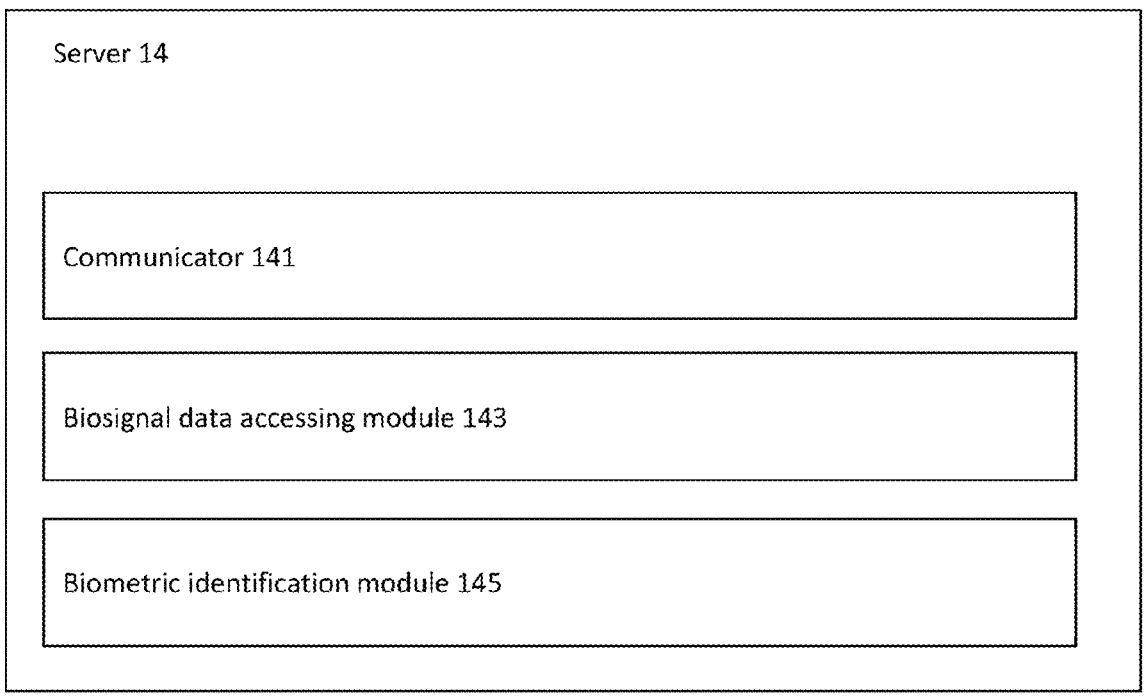
FIG. 8 shows a schematic diagram of an example data processing apparatus according to aspects of the present disclosure.

Referring to FIG. 8, there is shown a server/data processing apparatus 14 according to aspects of the present disclosure. The server 14 comprises a communicator 141 arranged to obtain, from a device, an identifier for a garment worn by a user. The server 14 comprises a biometric identification module 143 operable to determine from the biosignal data the biometric identity of the user wearing the garment. The communicator 141 is further arranged to transmit the biometric identity of the user to the device.

Figure 9:
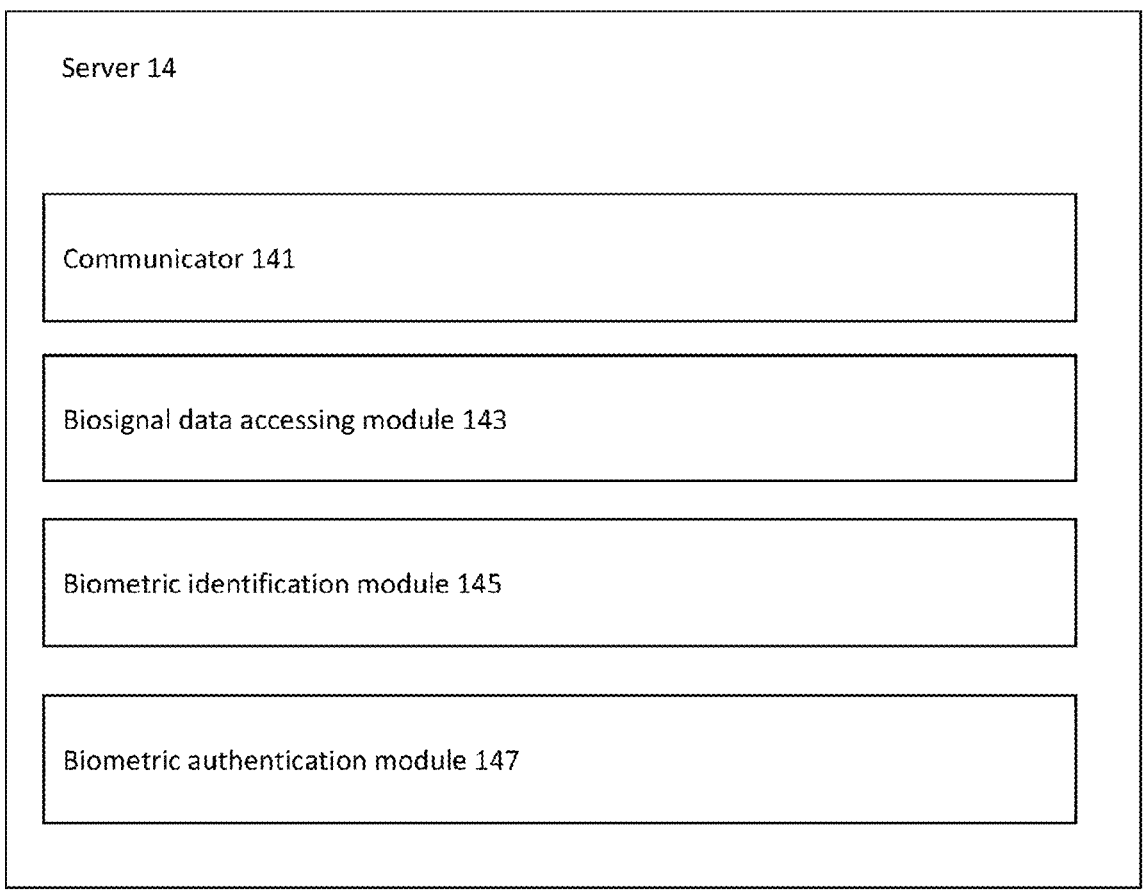
FIG. 9 shows a schematic diagram of another example data processing apparatus according to aspects of the present disclosure.

Referring to FIG. 9, there is shown another server/data processing apparatus 14 according to aspects of the present disclosure. The sever 14 comprises a communicator 141 arranged to obtain, from a device, an identifier for a garment worn by a user. The server 14 comprises a biosignal data accessing module 141 operable to access biosignal data sensed by the garment identified by the identifier. The server 14 comprises a biometric identification module 143 operable to determine from the biosignal data the biometric identity of the user wearing the garment. The server 14 comprises a biometric authentication module 145 operable to determine from the biometric identity whether the user has the authority to operate the device. The communicator 141 is further arranged to transmit, to the device, the result of the determination performed by the biometric authentication module.

Figure 10:
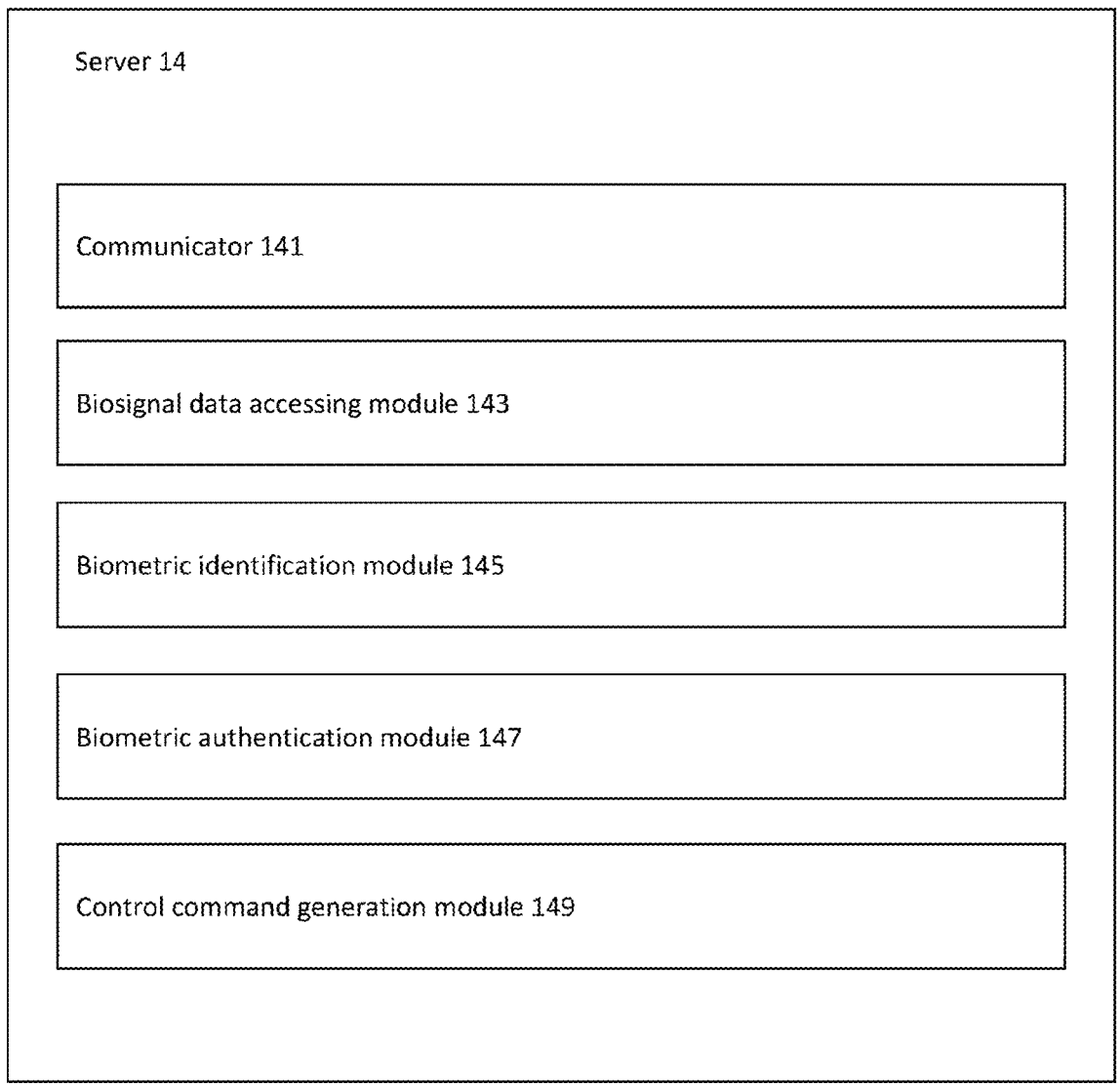
FIG. 10 shows a schematic diagram of another example data processing apparatus according to aspects of the present disclosure.

Referring to FIG. 10, there is shown another sever/data processing apparatus 14 according to aspects of the present disclosure. The sever 14 comprises a communicator 141 arranged to obtain, from a device, an identifier for a garment worn by a user. The server 14 comprises a biosignal data accessing module 143 operable to access biosignal data sensed by the garment identified by the identifier. The server 14 comprises a biometric identification module 145 operable to determine from the biosignal data the biometric identity of the user wearing the garment. The server 14 comprises a biometric authentication module 147 operable to determine from the biometric identity whether the user has the authority to operate the device. The server 14 further comprises a control command generation module 149 operable to generate a control command for controlling the device based on the determination of whether the user has the authority to operate the device. The communicator 141 is further arranged to transmit, to the device, the control command.

In the above examples, the biometric identity is used to determine whether the user is authorised to control the device. This is not required in all aspects of the present disclosure. Instead, and more generally, any form of operational mode for the device may be determined from the biometric identity. The operational mode may be an authorised to operate/not authorised to operate mode but is not required to be. Instead, the operational mode may relate to a preference or characteristic of the identified user wearing the garment.

In summary, there is provided a controller 161 for controlling a device 16. The controller 161 comprises an identifier obtaining module 165 arranged to obtain an identifier for a garment worn by a user. The controller 161 comprises a biometric module 167 arranged to use the identifier to obtain a biometric identity for the user wearing the identified garment and determine an operational mode for the device 16 from the biometric identity. A command generation module operable 169 to generate a control command for controlling the device based on the operational mode. The biometric module 167 may determine whether the user identified by the biometric identity is authorised to operate the device 16. The control command may be generated based on this determination.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A controller for controlling a computing device, the controller being configured to:
   obtain an identifier for a wearable device worn by a user by processing an image containing the wearable device, wherein the wearable device comprises a visual symbol which comprises the identifier, and the processing of the image containing the wearable device enables identifying the visual symbol and obtaining the identifier from the visual symbol, and wherein the computing device captures the image of the wearable device;
   use the identifier to obtain a biometric identity for the user wearing the identified wearable device, and determine an operational mode for the computing device from the biometric identity, wherein obtaining the biometric identity comprises causing the wearable device to transmit biosignal data sensed by the wearable device to a server, without the wearable device transmitting the biosignal data to the computing device thereby enhancing data security by preventing the computing device from accessing the biosignal data yet preserving the ability of the computing device to operate in the operational mode; and
   generate a control command for controlling the computing device based on the operational mode.

2. The controller as claimed in claim 1, wherein the controller is arranged to control the computing device to receive the identifier from the wearable device.

3. The controller as claimed in claim 2, wherein the controller is arranged to control the computing device to receive the identifier over a wireless network.

4. The controller as claimed in claim 1, wherein the controller is operable to determine the operational mode of the computing device by determining, from the biometric identity, whether the user has authority to operate the computing device, and wherein the controller is operable to generate the control command based on the determination of whether the user has the authority to operate the computing device.

5. The controller as claimed in claim 4, wherein the controller is operable to generate a control command which restricts the computing device from performing an operation when the user is not authenticated as having the authority to operate the computing device.

6. The controller as claimed in claim 4, wherein the controller is operable to generate a control command which allows the computing device to perform an operation when the user is authenticated as having the authority to operate the computing device.

7. The controller as claimed in claim 4, wherein the controller is arranged to determine, from the biometric identity, whether the user has the authority to operate the computing device by determining whether the biometric identity of the user corresponds to a pre-stored biometric identity for an authorised user.

8. The controller as claimed in claim 1, wherein the controller is arranged to use the identifier to access, via the server, the biosignal data sensed by the wearable device and process the accessed biosignal data to determine the biometric identity of the user.

9. The controller as claimed in claim 1, wherein the controller is arranged to control the computing device to transmit a request for the biometric identity of the user wearing the wearable device to the server, and control the computing device to receive, from the server, the biometric identity.

10. The controller as claimed in claim 1, wherein the controller is operable to control the computing device according to the generated control command.

11. The controller as claimed in claim 1, wherein the wearable device is a garment.

12. The controller as claimed in claim 1, wherein the computing device comprises the controller.

13. A computer implemented method comprising:
    obtaining an identifier for a wearable device worn by a user by processing an image containing the wearable device, wherein the wearable device comprises a visual symbol which comprises the identifier, and the processing of the image containing the wearable device enables identifying the visual symbol and obtaining the identifier from the visual symbol, and wherein a computing device captures the image of the wearable device;
    using the identifier to obtain a biometric identity for the user wearing the identified wearable device, wherein the biometric identity is obtained by causing the wearable device to transmit biosignal data sensed by the wearable device to a server, without the wearable device transmitting the biosignal data to the computing device thereby enhancing data security by preventing the computing device from accessing the biosignal data yet preserving the ability of the computing device to operate in an operational mode; and
    determining the operational mode for the computing device from the biometric identity; and
    generating a control command for controlling the computing device based on the determined operational mode.

14. The controller as claimed in claim 8, wherein the controller is arranged to receive biosignal data from a plurality of different wearable devices, and wherein the controller is arranged to use the identifier to determine which incoming biosignal data to access.

15. The controller as claimed in claim 14, wherein the incoming biosignal data is stored in a data store accessible by the controller, and wherein the controller is arranged to use the identifier obtained to determine which incoming biosignal data stored in the data store to access.

16. The method as claimed in claim 13, wherein determining the operational mode of the computing device comprises determining, from the biometric identity, whether the user has authority to operate the computing device, and wherein the control command is generated based on the determination of whether the user has the authority to operate the computing device.

17. The method as claimed in claim 13, further comprising:
    controlling the computing device to transmit a request for the biometric identity of the user wearing the wearable device to the server; and
    controlling the computing device to receive, from the server, the biometric identity.

18. A system comprising:
    a wearable device;
    a server; and
    a computing device comprising a controller configured to:
       obtain an identifier for a wearable device worn by a user by processing an image containing the wearable device, wherein the wearable device comprises a visual symbol which comprises the identifier, and the processing of the image containing the wearable device enables identifying the visual symbol and obtaining the identifier from the visual symbol, and wherein the computing device captures the image of the wearable device;

use the identifier to obtain a biometric identity for the user wearing the identified wearable device, wherein the biometric identity is obtained by causing the wearable device to transmit biosignal data sensed by the wearable device to the server, without the wearable device transmitting the biosignal data to the computing device thereby enhancing data security by preventing the computing device from accessing the biosignal data yet preserving the ability of the computing device to operate in an operational mode; and determine the operational mode for the computing device from the biometric identity; and generate a control command for controlling the computing device based on the determined operational mode.

* * * * *